(12) United States Patent
Fan et al.

(10) Patent No.: US 11,413,448 B2
(45) Date of Patent: *Aug. 16, 2022

(54) SOFT PHYSIOTHERAPY INSTRUMENT AND METHOD FOR USING THE SAME

(71) Applicant: Beijing FUNATE Innovation Technology Co., LTD., Beijing (CN)

(72) Inventors: Li Fan, Beijing (CN); Li Qian, Beijing (CN); Yu-Quan Wang, Beijing (CN)

(73) Assignee: Beijing FUNATE Innovation Technology Co., LTD., Beijing (CN)

( * ) Notice: Subject to any disclaimer, the term of this patent is extended or adjusted under 35 U.S.C. 154(b) by 407 days.

This patent is subject to a terminal disclaimer.

(21) Appl. No.: 16/739,224

(22) Filed: Jan. 10, 2020

(65) Prior Publication Data

US 2021/0106813 A1 Apr. 15, 2021

(30) Foreign Application Priority Data

Oct. 11, 2019 (CN) .......................... 201910965295.9

(51) Int. Cl.
*A61N 1/00* (2006.01)
*A61N 1/04* (2006.01)
*A61N 1/36* (2006.01)
*C01B 32/158* (2017.01)

(52) U.S. Cl.
CPC ............ *A61N 1/0488* (2013.01); *A61N 1/36* (2013.01); *C01B 32/158* (2017.08); *C01B 2202/08* (2013.01); *C01B 2202/34* (2013.01); *C01B 2202/36* (2013.01)

(58) Field of Classification Search
CPC .... A61N 1/0408; A61N 1/0476; A61N 1/048; A61N 1/0484; A61N 1/0488; A61N 1/328; A61N 1/36; A61N 1/3603; A45D 44/002
See application file for complete search history.

(56) References Cited

U.S. PATENT DOCUMENTS

| 11,229,791 B2* | 1/2022 | Fan ................. A61N 1/0484 |
| 11,260,217 B2* | 3/2022 | Fan ................. A61N 1/0408 |
| 2009/0085461 A1 | 4/2009 | Feng et al. |
| 2009/0153506 A1 | 6/2009 | Liu et al. |
| 2012/0250908 A1 | 10/2012 | Jiang et al. |
| 2013/0110215 A1 | 5/2013 | Fan et al. |
| 2015/0282534 A1 | 10/2015 | Jiang et al. |

(Continued)

FOREIGN PATENT DOCUMENTS

| CN | 106334269 A | * | 1/2017 | ............. A61N 2/002 |
| CN | 107260390 | | 10/2017 | |
| CN | 107616911 | | 1/2018 | |

(Continued)

*Primary Examiner* — Brook Kebede
(74) *Attorney, Agent, or Firm* — ScienBiziP, P.C.

(57) ABSTRACT

A soft physiotherapy instrument includes a flexible sheet and a controller. The flexible sheet includes a first flexible layer, a second flexible layer, a plurality of functional layers located between the first flexible layer and the second flexible layer, and a plurality of electrodes electrically connected with the plurality of functional layers. The functional layer includes a carbon nanotube layer including a plurality of carbon nanotubes uniformly distributed. The flexible sheet is electrically coupled with the controller via the plurality of electrodes. A method for using the soft physiotherapy instrument is further provided.

19 Claims, 14 Drawing Sheets

(56) References Cited

U.S. PATENT DOCUMENTS

2016/0023908 A1   1/2016   Jiang et al.
2019/0105486 A1   4/2019   Guido et al.

FOREIGN PATENT DOCUMENTS

| CN | 207168836 | 4/2018 |
|---|---|---|
| CN | 108159563 | 6/2018 |
| CN | 208838309 | 5/2019 |
| CN | 109984944 | 7/2019 |
| CN | 209435460 U | 9/2019 |
| JP | 2009-146424 | 7/2009 |
| JP | 2010-18515 | 1/2010 |
| JP | 2012-130484 | 7/2012 |
| JP | 2014-146478 | 8/2014 |
| JP | 2014-231453 | 12/2014 |
| JP | 2015-47382 | 3/2015 |
| JP | 2017-108758 | 6/2017 |
| JP | 2018-187364 | 11/2018 |
| KR | 10-2004-0073928 | 8/2004 |
| TW | I608994 | 12/2017 |
| WO | 2015145195 | 10/2015 |

* cited by examiner

SOFT PHYSIOTHERAPY INSTRUMENT AND METHOD FOR USING THE SAME

CROSS-REFERENCE TO RELATED APPLICATIONS

The application is also related to applications entitled, "METHOD FOR USING BEAUTY INSTRUMENT WITH MASK", filed Jan. 10, 2020 (Ser. No. 16/739,206); "BEAUTY INSTRUMENT WITH MASK", filed Jan. 10, 2020 (Ser. No. 16/739,210); "METHOD FOR USING BEAUTY INSTRUMENT WITH MASK", filed Jan. 10, 2020 (Ser. No. 16/739,212); "BEAUTY INSTRUMENT WITH MASK", filed Jan. 10, 2020 (Ser. No. 16/739,203).

FIELD

The subject matter herein generally relates to a soft physiotherapy instrument and method for using the same.

BACKGROUND

As the living standards being improved, demands for health are becoming greater. As such, products of physiotherapy are popular and sell well. However, most of the physiotherapy products on market are hard material physiotherapy devices with a small working area, which may cause discomfort on skin of users.

BRIEF DESCRIPTION OF THE DRAWINGS

Implementations of the present technology will now be described, by way of embodiments, with reference to the attached figures, wherein.

DETAILED DESCRIPTION

Figure 1:
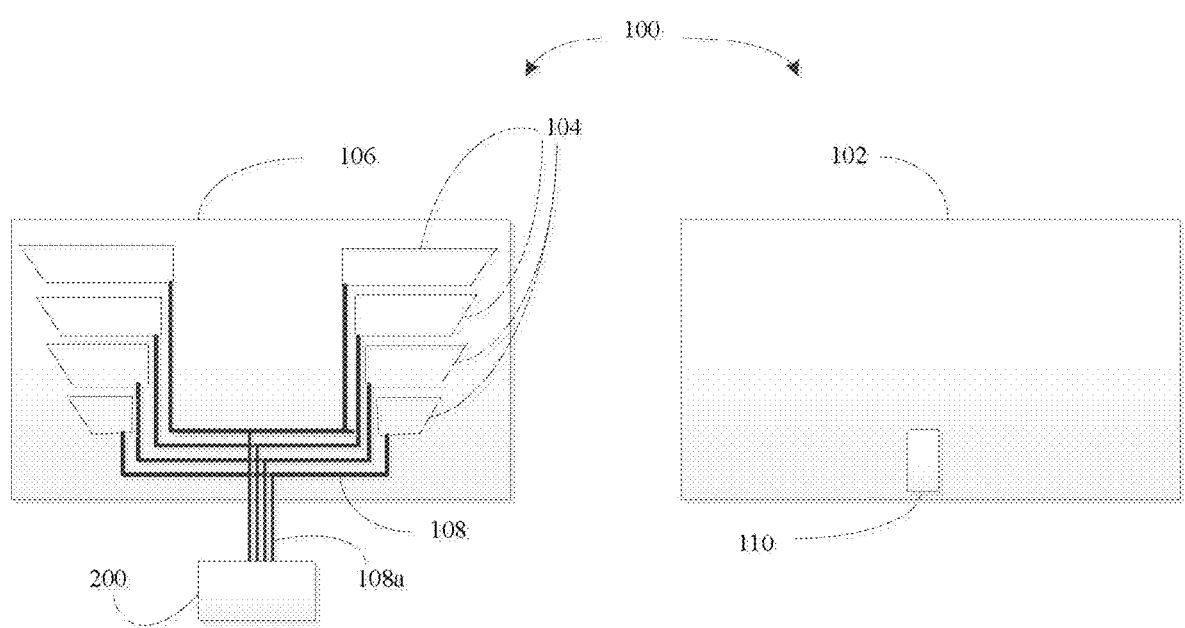
FIG. 1 is a schematic view of a soft physiotherapy instrument according to a first embodiment.
Figure 2:
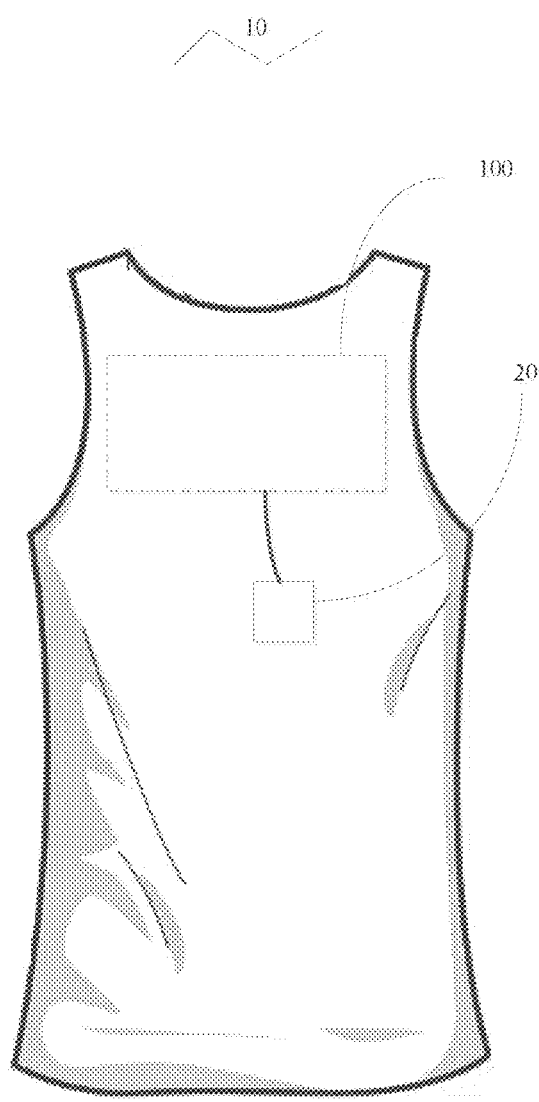
FIG. 2 is a schematic view of a clothes using the soft physiotherapy instrument according to one embodiment.
Figure 3:
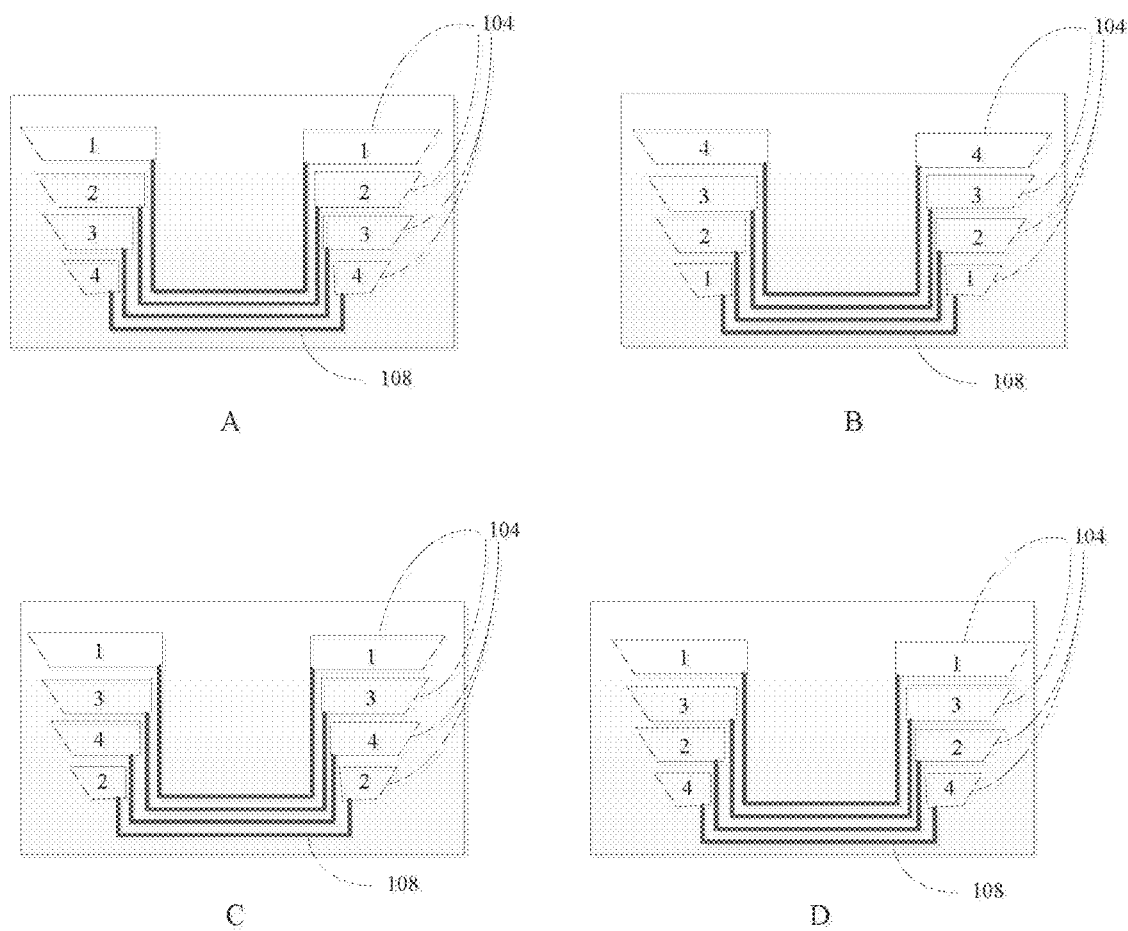
FIG. 3 shows schematic views of functional layers' numberings in the soft physiotherapy instrument provided by the first embodiment.

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean "at least one."

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented.

The term "contact" is defined as a direct and physical contact. The term "substantially" is defined to be that while essentially conforming to the particular dimension, shape, or other feature that is described, the component is not or need not be exactly conforming to the description. The term "comprising," when utilized, means "including, but not necessarily limited to"; it specifically indicates open-ended inclusion or membership in the so-described combination, group, series, and the like.

Referring to FIG. 1, a soft physiotherapy instrument (not labeled) according to a first embodiment is provided. The soft physiotherapy instrument includes a flexible sheet 100 and a controller 200 for controlling the flexible sheet 100. The flexible sheet 100 includes a first flexible layer 102 and a second flexible layer 106 overlapped with each other (for clarity of display, in FIG. 1, the first flexible layer 102 and the second flexible layer 106 are separately shown), a plurality of functional layers 104 sandwiched between the first flexible layer 102 and the second flexible layer 106, the plurality of functional layers 104 are symmetrically distributed or regularly distributed, and a plurality of electrodes 108, each of the plurality of electrodes 108 is electrically connected with a single functional layer 104 or a pair of functional layers 104. If a quantity of the plurality of electrodes 108 is defined as K (K=1, 2, 3, 4, 5 . . . ), then a quantity of the plurality of functional layers 104 is 2K (K=1, 2, 3, 4, 5 . . . ) or K. The controller is electrically connected to the K electrodes 108, and the plurality of functional layers 104 in the flexible sheet 100 are controlled by the K electrodes 108. In one embodiment, according to FIG. 1, the quantity of the plurality of functional layers 104 is 8 (2K), for example, the quantity of the plurality of electrodes 108 is 4 (K). Each electrode 108 is electrically connected with two functional layers 104. Two ends of the electrode 108 are separately connected with the two functional layers 104. The two functional layers 104 electrically connected with the electrode 108 are symmetrically located. Each of the plurality of functional layers 104 is a carbon nanotube layer.

The plurality of functional layers 104 comprises two or more functional layers 104. As shown in FIG. 1, the flexible sheet 100 includes 8 functional layers 104. The 8 functional layers 104 are symmetrically distributed in the flexible sheet 100. When the flexible sheet 100 includes a plurality of functional layers 104, the position of the functional layer 104 is not limited. The number of the functional layers 104 is not limited and can be adjusted as needed, and may be 2, 8, 15, 20, or the like. An area of each functional layer 104 is not limited and can be adjusted as needed. Adjacent functional layers 104 are spaced apart and insulated from each other.

The controller 200 includes a plurality of function buttons for controlling the flexible sheet 100. The controller 200 is electrically connected to the flexible sheet 100 through the plurality of electrodes 108. The controller 200 is used to input a voltage between two of the plurality of electrodes 108 to produce a current in the plurality of functional layers 104. A circuit is formed between the controller 200, the two of the plurality of electrodes 108, the plurality of functional layers 104 electrically connected with the two of the plurality of electrodes 108, and skin of a user. As such, the current flows through the controller 200, the two of the plurality of electrodes 108, the plurality of functional layers 104 electrically connected with the two of the plurality of electrodes 108, and the skin of the user. Each of the plurality of function buttons can control a current magnitude, a frequency of the current, a position of the input current, etc., to control the plurality of functional layers 104 inside the flexible sheet 100. The flexible sheet 100 can be movably coupled to the controller 200. Optionally, the first flexible layer 102 or the second flexible layer 106 can include a window 110, and the plurality of electrodes 108 are exposed from the window 110 and electrically connected to the controller 200 via a plurality of electrode lead wires 108a. The window 110 is provided with an access port through which the controller 200 is connected to the flexible sheet 100. The flexible sheet 100 can be replaced as needed. The flexible sheet 100 can also be cleaned for reuse.

A material of the first flexible layer 102 or the second flexible layer 106 can be a flexible material such as non-woven fabric, silk, flexible cloth, porous flexible paper, or silica gel, and can be directly attached to the user's skin. A thickness of the first flexible layer 102 or the second flexible layer 106 can be set according to actual needs. In this embodiment, the thickness of the first flexible layer 102 or the second flexible layer 106 is in a range from 10 to 100 micrometers. In use of the soft physiotherapy instrument, the second flexible layer 106 will be directly attached on the skin of the user. The second flexible layer 106 is a porous structure.

A material of the electrode 108 can be metal, alloy, indium tin oxide (ITO), antimony tin oxide (ATO), conductive silver paste, conductive polymer, or conductive carbon nanotube. The metal or the alloy can be aluminum, copper, tungsten, molybdenum, gold, titanium, rhodium, palladium, iridium or any alloy thereof. In this embodiment, the K electrodes 108 are all copper wires with a diameter of 1 micrometer. Preferably, an insulating layer can be coated on the surface of each of the K electrodes 108. A material of the insulating layer can be a flexible material.

Each electrode 108 corresponds to one functional layer 104 or two functional layers 104. When one electrode 108 corresponds to one functional layer 104, one end of the electrode 108 is electrically connected to the functional layer 104, and the other end is electrically connected to the controller 200. In this case, the controller 200 can control the one functional layer 104 through the one electrode 108. The numbering of the one electrode 108 corresponds to the numbering of the one functional layer 104. When one electrode 108 corresponds to two functional layers 104, two ends of the electrode 108 are separately electrically connected to the two functional layers 104, and a middle part of the electrode 108 is electrically connected to the controller 200. In this case, the controller 200 can control the two functional layers 104 simultaneously, and the numbering of the one electrode 108 corresponds to the numbering of a pair of functional layers 104. The two functional layers 104 electrically connected with the same electrode 108 have the same numbering. The numbering order of the plurality of electrodes 108 does not represent the position order. That is, the positions of two electrodes 108 with neighbor numbering may be adjacently or at intervals. Since the numbering of the electrode 108 corresponds to the numbering of the functional layer 104, it can be understood that the positions of two pairs of adjacent functional layers 104 or the two adjacent functional layers 104 with neighbor numbering may be adjacently or at intervals. Referring to FIG. 1, in this embodiment, one electrode 108 corresponds to a pair of functional layers 104, and the flexible sheet 100 includes four pairs of functional layers 104. Referring to FIGS. 3A to 3D, for example, the four pairs of functional layers 104 are numbered 1, 2, 3, and 4, positions 1, 2, 3, and 4 can be arbitrarily set.

The carbon nanotube layer includes a plurality of carbon nanotubes joined by van der Waals attractive force therebetween. The carbon nanotube layer can be a substantially pure structure of carbon nanotubes, with few impurities. The carbon nanotube layer can be a freestanding structure, that is, the carbon nanotube layer can be supported by itself without a substrate. For example, if at least one point of the carbon nanotube layer is held, the entire carbon nanotube layer can be lifted while remaining its structural integrity.

The carbon nanotubes in the carbon nanotube layer can be orderly or disorderly arranged. The term 'disordered carbon nanotube layer' refers to a structure where the carbon nanotubes are arranged along different directions, and the aligning directions of the carbon nanotubes are random. The number of the carbon nanotubes arranged along each different direction can be almost the same (e.g. uniformly disordered). The disordered carbon nanotube layer can be isotropic, namely the carbon nanotube layer has properties identical in all directions of the carbon nanotube layer. The carbon nanotubes in the disordered carbon nanotube layer can be entangled with each other.

The carbon nanotube layer including ordered carbon nanotubes is an ordered carbon nanotube layer. The term 'ordered carbon nanotube layer' refers to a structure where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions). The carbon nanotubes in the carbon nanotube layer can be selected from single-walled, double-walled, and/or multi-walled carbon nanotubes. The carbon nanotube layer may include at least one carbon nanotube film. In other embodiments, the carbon nanotube layer is composed of one carbon nanotube film or at least two carbon nanotube films. In other embodiment, the carbon nanotube layer consists one carbon nanotube film or at least two carbon nanotube films.

Figure 4:
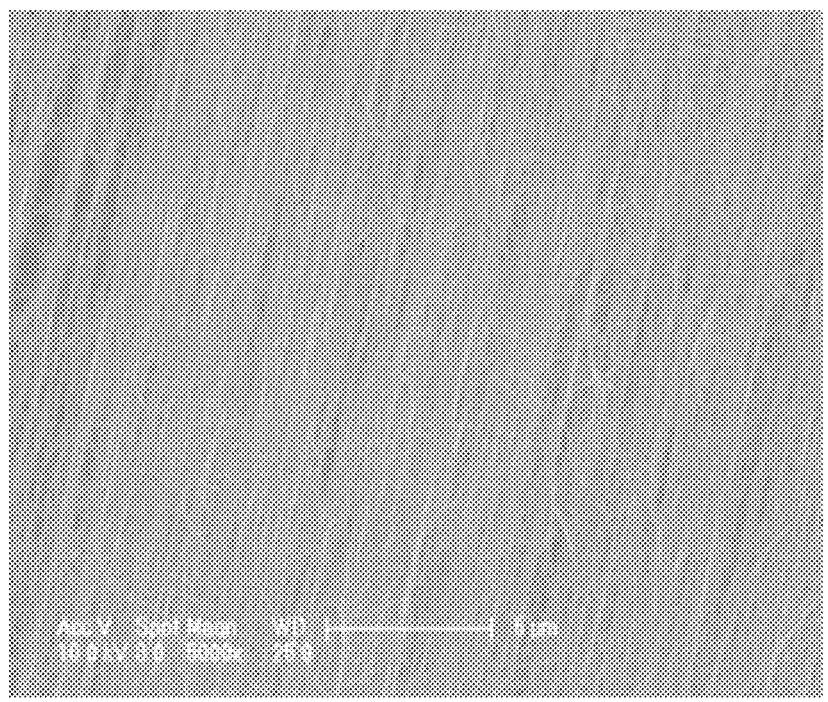
FIG. 4 shows a Scanning Electron Microscope (SEM) image of a drawn carbon nanotube film.
Figure 5:
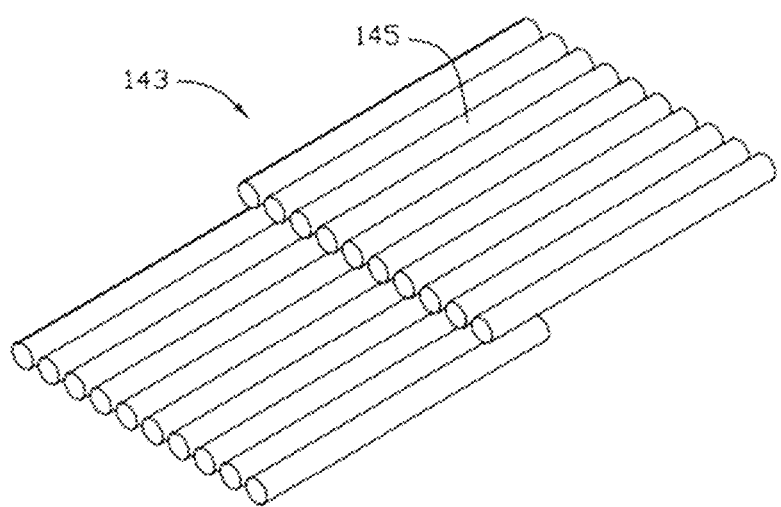
FIG. 5 is a schematic view of carbon nanotube segments in the drawn carbon nanotube film.

In one embodiment, the carbon nanotube film can be a drawn carbon nanotube film. Referring to FIG. 4, the drawn carbon nanotube film includes a number of successive and oriented carbon nanotubes joined end-to-end by van der Waals attractive force therebetween. The drawn carbon nanotube film is a freestanding film. Each drawn carbon nanotube film includes a number of successively oriented carbon nanotube segments joined end-to-end by van der Waals attractive force therebetween. Referring to FIG. 5, each carbon nanotube segment 143 includes a number of carbon nanotubes 145 substantially parallel to each other, and joined by van der Waals attractive force therebetween. Some variations can occur in the drawn carbon nanotube film. The carbon nanotubes in the drawn carbon nanotube film are oriented along a preferred orientation. The drawn carbon nanotube film can be treated with an organic solvent to increase mechanical strength and toughness of the drawn carbon nanotube film and reduce coefficient of friction of the drawn carbon nanotube film. A thickness of the drawn carbon nanotube film may range from about 0.5 nanometers to about 100 micrometers. The drawn carbon nanotube film can be used as a carbon nanotube layer directly.

The carbon nanotubes in the drawn carbon nanotube film can be single-walled, double-walled, and/or multi-walled carbon nanotubes. The diameters of the single-walled carbon nanotubes may range from about 0.5 nanometers to about 50 nanometers. The diameters of the double-walled carbon nanotubes may range from about 1 nanometer to about 50 nanometers. The diameters of the multi-walled carbon nanotubes may range from about 1.5 nanometers to about 50 nanometers. The lengths of the carbon nanotubes may range from about 200 micrometers to about 900 micrometers.

The carbon nanotube layer may include at least two stacked drawn carbon nanotube films. The carbon nanotubes in the drawn carbon nanotube film are aligned along one preferred orientation, an angle can exist between the orientations of carbon nanotubes in adjacent drawn carbon nanotube films, whether stacked or adjacent. An angle between the aligned directions of the carbon nanotubes in two adjacent drawn carbon nanotube films may range from about 0 degrees to about 90 degrees (e.g. about 15 degrees, 45 degrees or 60 degrees).

Figure 6:
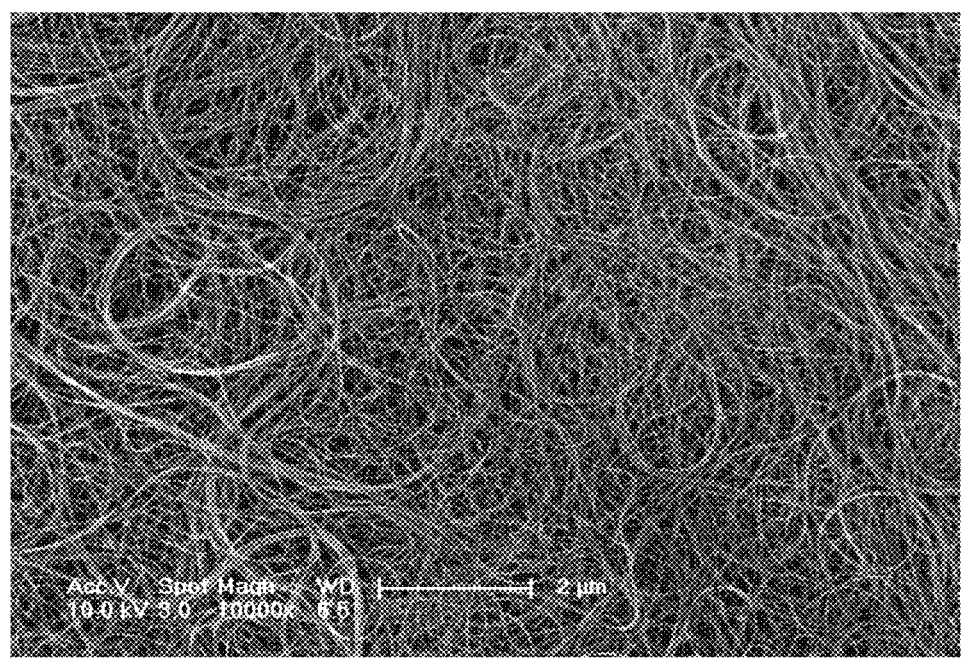
FIG. 6 shows an SEM image of a flocculated carbon nanotube film.

In other embodiments, the carbon nanotube film can be a flocculated carbon nanotube film. Referring to FIG. 6, a flocculated carbon nanotube film may include a plurality of long, curved, and disordered carbon nanotubes entangled with each other. Furthermore, the flocculated carbon nanotube film can be isotropic. The carbon nanotubes can be substantially uniformly dispersed in the flocculated carbon nanotube film. Adjacent carbon nanotubes are acted upon by van der Waals attractive force to obtain an entangled structure with micropores defined therein. Because the carbon nanotubes in the flocculated carbon nanotube film are entangled with each other, the carbon nanotube layer employing the flocculated carbon nanotube film has excellent durability, and can be fashioned into desired shapes with a low risk to the integrity of the carbon nanotube layer. A thickness of the flocculated carbon nanotube film may range from about 0.5 nanometers to about 1 millimeter.

Figure 7:
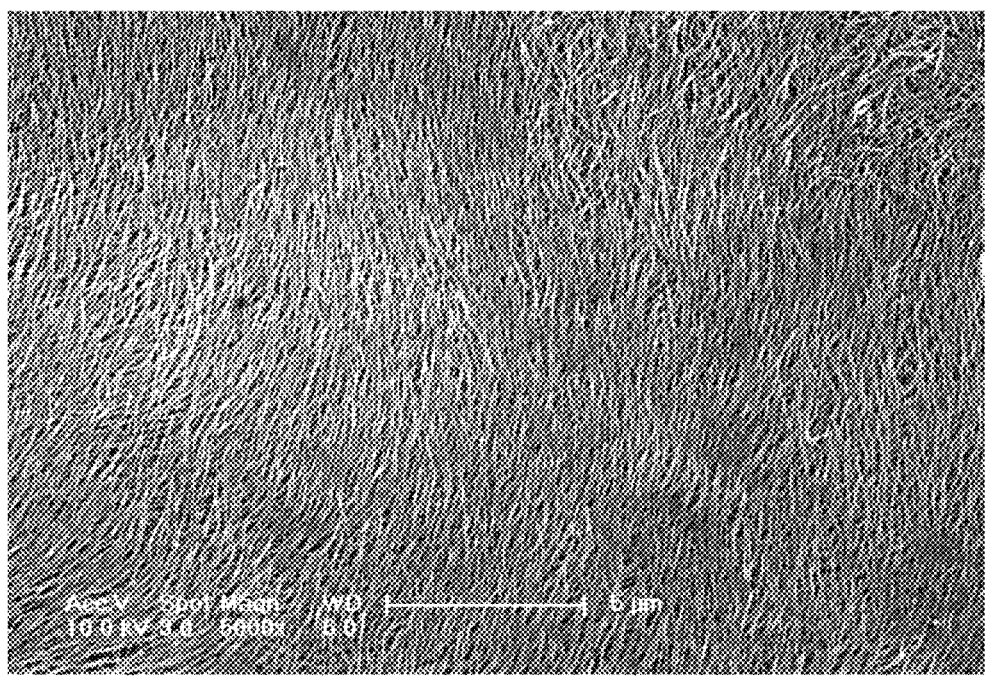
FIG. 7 shows an SEM image of a pressed carbon nanotube film.

Referring to FIG. 7, in other embodiments, the carbon nanotube film can be a pressed carbon nanotube film. The pressed carbon nanotube film is formed by pressing a carbon nanotube array. The carbon nanotubes in the pressed carbon nanotube film are arranged along a same direction or along different directions. The carbon nanotubes in the pressed carbon nanotube film can rest upon each other. Adjacent carbon nanotubes are attracted to each other and are joined by van der Waals attractive force. An angle between a primary alignment direction of the carbon nanotubes and a surface of the pressed carbon nanotube film is in a range from 0 degrees to 15 degrees. The greater the pressure applied, the smaller the angle obtained. In one embodiment, the carbon nanotubes in the pressed carbon nanotube film are arranged along different directions, the carbon nanotube layer can be isotropic. A thickness of the pressed carbon nanotube film may range from about 0.5 nanometers to about 1 millimeter.

Figure 8:
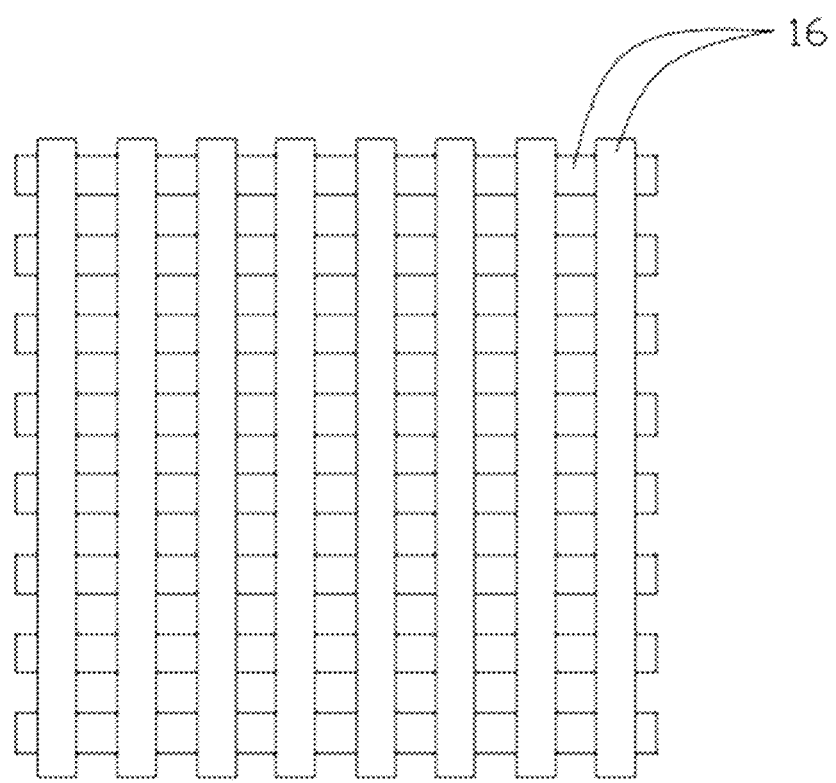
FIG. 8 is a schematic view of a functional layer including a plurality of carbon nanotube wires crossed with each other.
Figure 9:
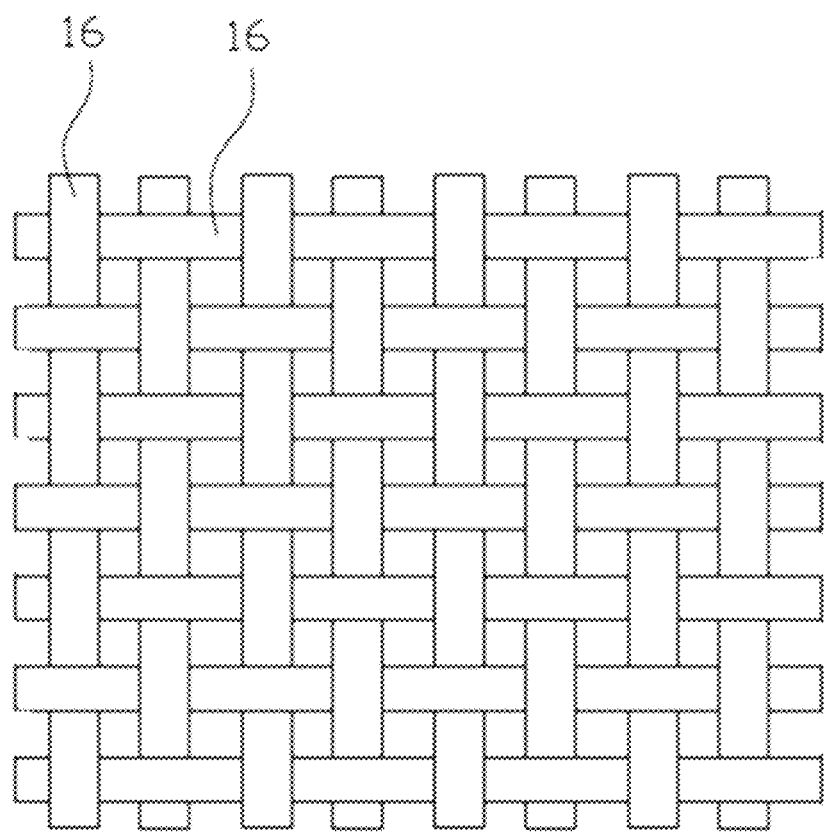
FIG. 9 is a schematic view of a functional layer including a plurality of carbon nanotube wires weaved with each other.
Figure 10:
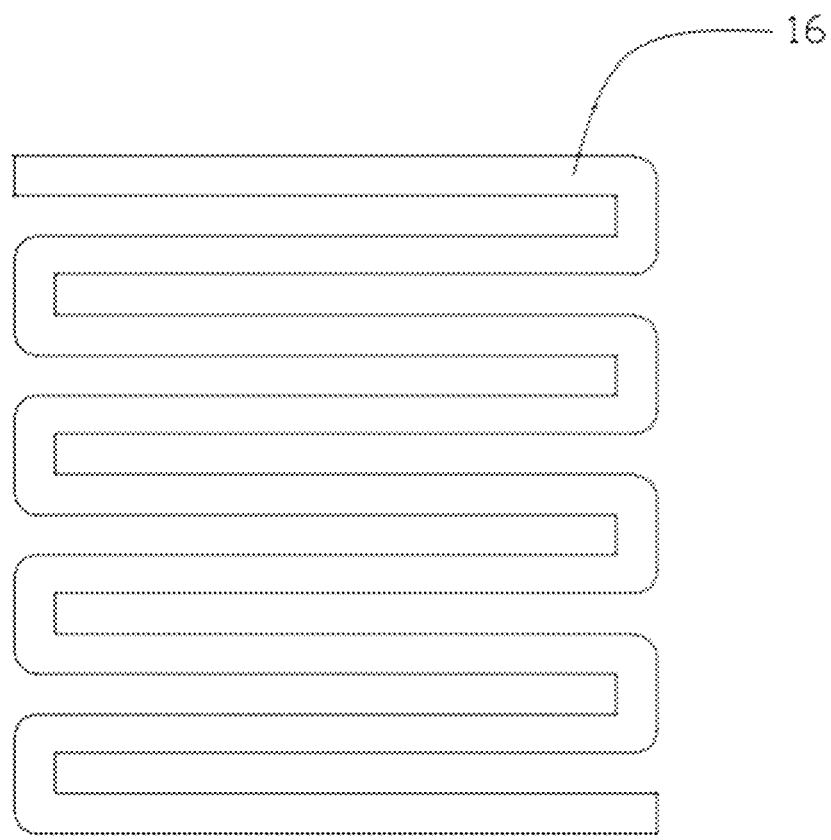
FIG. 10 is a schematic view of a functional layer including a bended and winded carbon nanotube wire.

In some embodiments, the carbon nanotube layer may include a plurality of carbon nanotube wires. Referring to FIG. 8, a plurality of carbon nanotube wires 16 can be crossed with each other to form the carbon nanotube layer. Referring to FIG. 9, a plurality of carbon nanotube wires 16 can be waved with each other to form the carbon nanotube layer. In other embodiments, the carbon nanotube layer can include only one carbon nanotube wire. Referring to FIG. 10, a carbon nanotube wire 16 can be bended to form the carbon nanotube layer.

Figure 11:
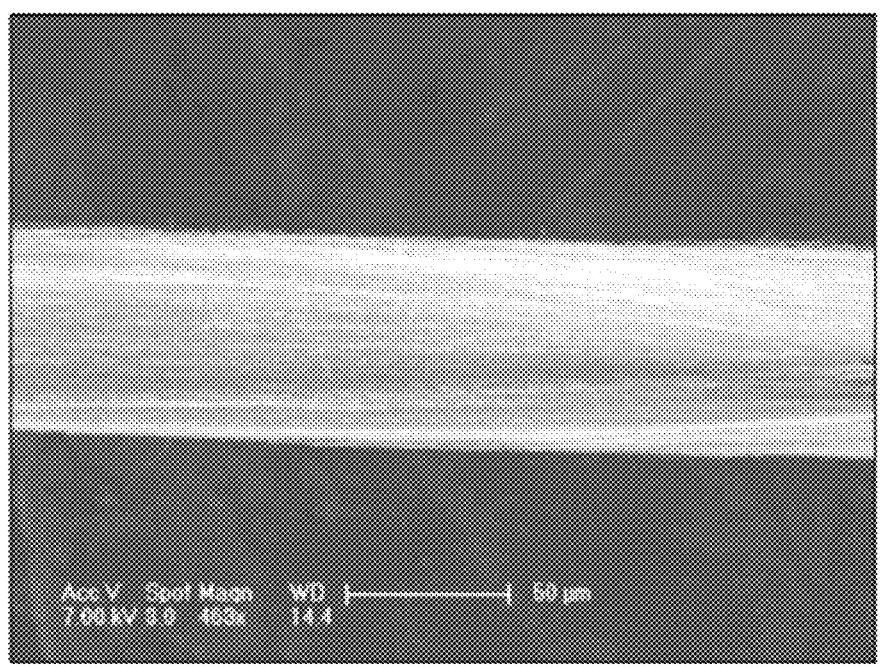
FIG. 11 is an SEM image of an untwisted carbon nanotube wire.

The carbon nanotube wire can be untwisted or twisted. Referring to FIG. 11, an untwisted carbon nanotube wire includes a plurality of carbon nanotubes substantially oriented along a same direction (i.e., a direction along the length direction of the untwisted carbon nanotube wire). The untwisted carbon nanotube wire can be a pure structure of carbon nanotubes. The untwisted carbon nanotube wire can be a freestanding structure. The carbon nanotubes are substantially parallel to the axis of the untwisted carbon nanotube wire. In one embodiment, the untwisted carbon nanotube wire may include a plurality of successive carbon nanotube segments joined end to end by van der Waals attractive force therebetween. Each carbon nanotube segment may include a plurality of carbon nanotubes substantially parallel to each other, and combined by van der Waals attractive force therebetween. The carbon nanotube segments can vary in width, thickness, uniformity, and shape. The length of the untwisted carbon nanotube wire can be arbitrarily set as desired. A diameter of the untwisted carbon nanotube wire may range from about 50 nanometers to about 100 micrometers.

Figure 12:
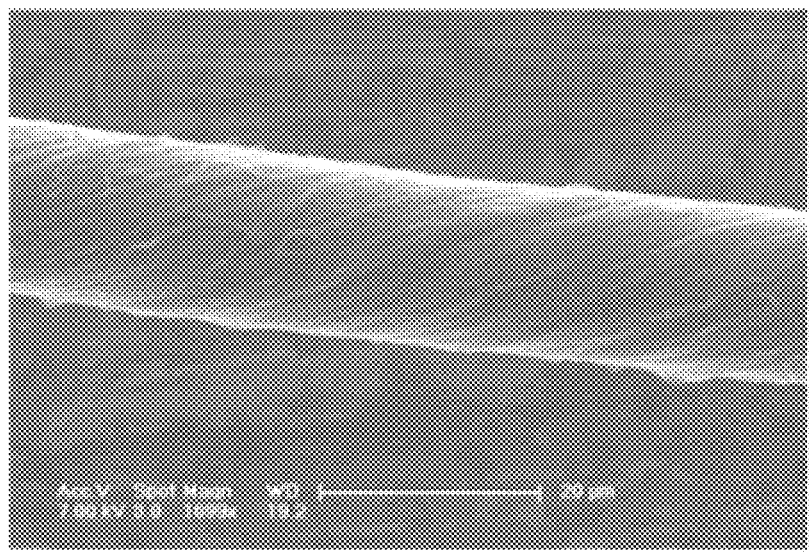
FIG. 12 is an SEM image of a twisted carbon nanotube wire.

Referring to FIG. 12, a twisted carbon nanotube wire may include a plurality of carbon nanotubes helically oriented around an axial direction of the twisted carbon nanotube wire. The twisted carbon nanotube wire can be a pure structure of carbon nanotubes. The twisted carbon nanotube wire can be a freestanding structure. In one embodiment, the twisted carbon nanotube wire may include a plurality of successive carbon nanotube segments joined end to end by van der Waals attractive force therebetween. Each carbon nanotube segment may include a plurality of carbon nanotubes substantially parallel to each other, and combined by van der Waals attractive force therebetween. The length of the carbon nanotube wire can be set as desired. A diameter of the twisted carbon nanotube wire may range from about 50 nanometers to about 100 micrometers. Furthermore, the twisted carbon nanotube wire can be treated with a volatile organic solvent after being twisted. After being soaked by the organic solvent, the adjacent substantially parallel carbon nanotubes in the twisted carbon nanotube wire will bundle together, due to a surface tension of the organic solvent when the organic solvent volatilizes. The density and strength of the twisted carbon nanotube wire will increase.

The carbon nanotube layer has a better flexibility than the first flexible layer and/or the second flexible layer. When the carbon nanotube layer is used as the functional layer in the flexible sheet, the flexibility of the entire flexible sheet is not decreased by the functional layer. The carbon nanotube layer has a large strength, as such, no matter how the flexible sheet is bent or pulled, and the carbon nanotube layer is not damaged.

A soft physiotherapy instrument according to a second embodiment is provided. The soft physiotherapy instrument comprises a flexible sheet and a controller. Referring to FIG.

Figure 13:
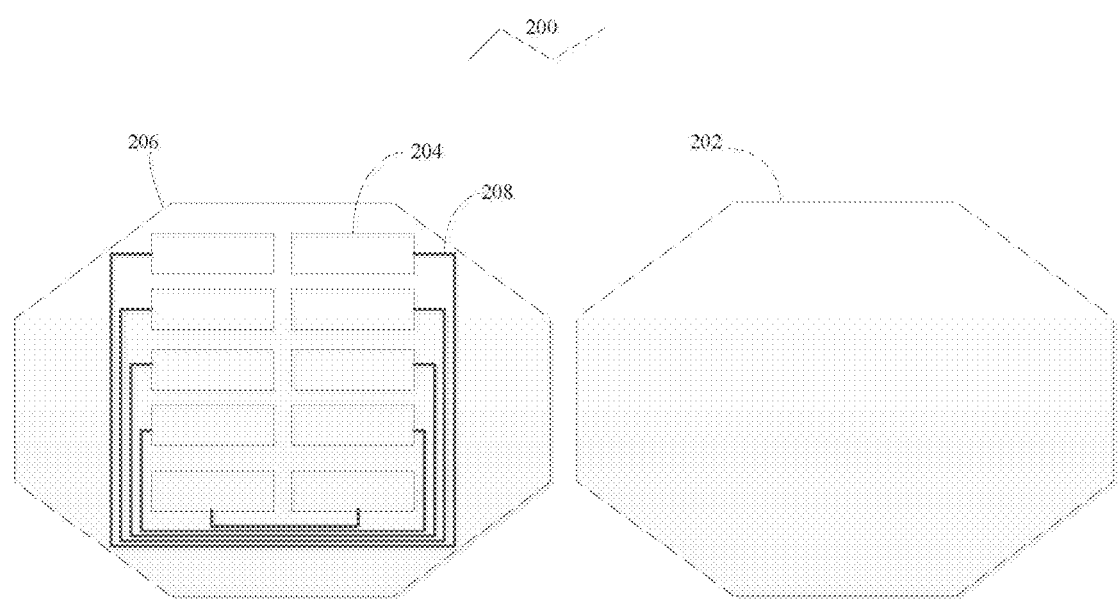
FIG. 13 is a schematic view of a soft physiotherapy instrument according to a second embodiment.

13, a flexible sheet 200 includes a first flexible layer 202 and a second flexible layer 206, the first flexible layer 202 and the second flexible layer 206 are stacked with each other. The flexible sheet 200 further includes a plurality of functional layers 204 sandwiched between the first flexible layer 202 and the second flexible layer 206 and a plurality of electrodes 208 electrically connected with the plurality of functional layers 204. In this embodiment, a quantity of the plurality of functional layers 204 is 10, and a quantity of the plurality of electrodes 208 is 5. A shape of the flexible sheet 200 is hexagon. Just can be seen form FIG. 13, there are 10 functional layers symmetrically distributed.

Other characteristics of the soft physiotherapy instrument in the second embodiment are the same as that of the soft physiotherapy instrument in the first embodiment.

Figure 14:
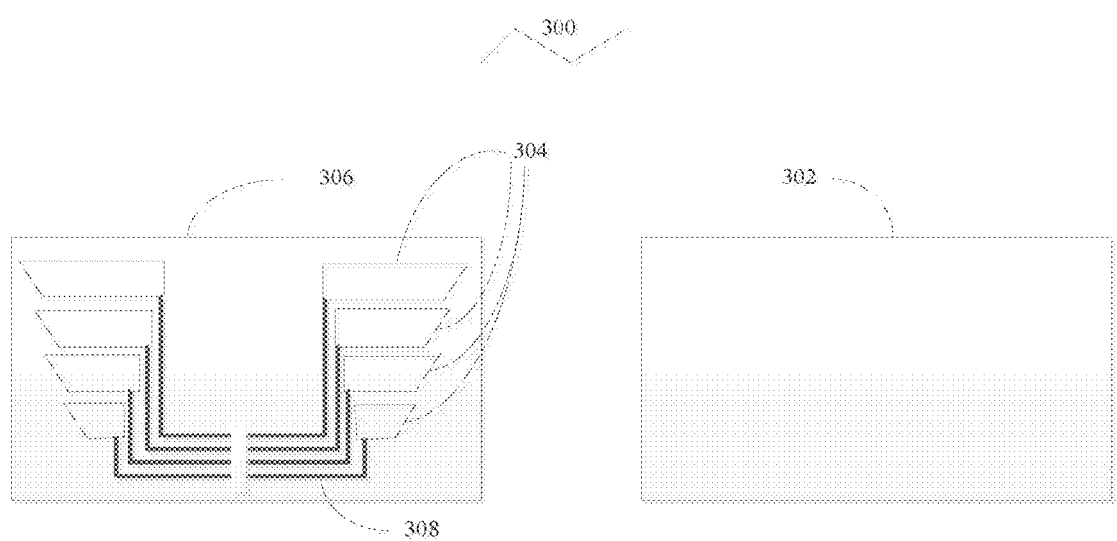
FIG. 14 is a schematic view of a soft physiotherapy instrument according to a third embodiment.

A soft physiotherapy instrument according to a third embodiment is provided. The soft physiotherapy instrument comprises a flexible sheet and a controller. Referring to FIG. 14, a flexible sheet 300 includes a first flexible layer 302 and a second flexible layer 306, the first flexible layer 302 and the second flexible layer 306 are stacked with each other. The flexible sheet 300 further includes a plurality of functional layers 304 sandwiched between the first flexible layer 302 and the second flexible layer 306 and a plurality of electrodes 308 electrically connected with the plurality of functional layers 304. In this embodiment, each of the plurality of electrodes 308 is electrically connected with a single functional layer 304. As shown in FIG. 14, there are 8 functional layers 304 symmetrically distributed, and 8 electrodes 308 are electrically connected with the 8 functional layers 304 in a one by one manner.

Other characteristics of the soft physiotherapy instrument in the third embodiment are the same as that of the soft physiotherapy instrument in the first embodiment.

The present invention further provides a method of using a soft physiotherapy instrument, the method comprises the steps of:

Step S1: providing a soft physiotherapy instrument, the soft physiotherapy instrument comprises a flexible sheet and a controller;

Step S2: applying the flexible sheet on a user's skin; and

Step S3: turning on the controller and selecting a function button on the controller, inputting a current to a plurality of functional layer in the flexible sheet, and stimulating skin with the current.

In step S1, the soft physiotherapy instrument is any one of the soft physiotherapy instruments discussed above.

Alternatively, before step S2, the flexible sheet can be further infiltrated with a liquid, that is, before the flexible sheet of the soft physiotherapy instrument is applied on the user's skin. The liquid can be a medicine liquid.

In step S3, the controller includes a plurality of function buttons for controlling the flexible sheet. Each of the plurality of function buttons is used to control the functional layer inside the flexible sheet to achieve the stimulating function. Each of the plurality of function buttons can be configured to control a current magnitude, a current frequency, a position of the functional layer which the current is input. The controller can input current to at least two functional layers via two electrodes. As such, the controller can control the functional layer inside the flexible sheet to simultaneously stimulate the skin, or selectively control a certain functional layer or some certain functional layers to simultaneously stimulate the skin.

In use of the soft physiotherapy instrument, a voltage is applied to two pairs of functional layers or two functional layers via two electrodes, and a micro-current will be input through the two electrode to the two pairs of functional layers or the two functional layers, and skin between or under the two pairs of functional layers or the two functional layers will be stimulated by the micro-current. The voltage applied on each two electrodes can be kept for a power-on time, and the voltage is stop for a dwell time, then the voltage is applied to another two electrodes for another power-on time and another dwell time. The voltage can be applied to two electrodes in an order 1 and 2, 2 and 3, 3 and 4 . . . K−1 and K (K is the numbering of each electrode), so that the two pairs of functional layers corresponding to each two electrodes are cyclically input current, and the skin corresponding the two pairs of functional layers are cyclically stimulated. The numbers of the two pairs of functional layers are adjacent, such as numbers 2 and 3, which does not mean that the positions of the two pairs of functional layers are adjacent. The positions of the two pairs of functional layers adjacent to each other can be arbitrarily set according to actual needs. Referring to FIG. 3A to FIG. 3D, in these embodiments, each electrode 108 corresponds to a pair of functional layers 104, and the flexible sheet 100 includes four pairs of functional layers 104. The four electrodes 108 are numbered 1, 2, 3, and 4, and the four pairs of functional layers 104 are numbered 1, 2, 3, and 4. Positions 1, 2, 3, and 4 can be arbitrarily set, for example, 3A to 3D in FIG. 3. In the application, the electrodes 108 are energized according to the circulation pattern of the electrodes numbered 1 and 2, 2 and 3, and 3 and 4, thereby sequentially or selectively generating micro-currents in the two pairs of functional layers, which in turn stimulate the skin.

In one embodiment according to FIG. 3B, in use of the soft physiotherapy instrument, the electrodes 108 are energized according to the circulation pattern of the electrodes numbered 1 and 2, 2 and 3, and 3 and 4, thereby sequentially or selectively generating micro-currents in the two pairs of functional layers, which in turn stimulate the skin. A working time of each pair of electrodes 108 is defined, during the working time, an alternating current (AC) is applied on the each pair of electrodes 108.

The flexible sheet can be movably coupled to the controller. The flexible sheet defines an access at the window position on the first flexible layer or the second flexible layer, and the controller is connected to the flexible sheet through the access. The flexible sheet can be changed as needed. The flexible sheet can also be cleaned to achieve re-use purpose.

Compared with the prior art, the soft physiotherapy instrument provided by the present invention has the following advantages: First, the flexible sheet has a strong flexibility due to the use of carbon nanotube materials, which can be directly attached to human skin, and the human body has a strong sense of comfort. Second, because the carbon nanotube material can be made into any area as required, the area of the flexible sheet can be set freely, the area acting on the human body can be set as needed, or it can be directly made into a physical therapy clothing. The soft physiotherapy instrument has a wider range of applications. Third, the carbon nanotube layer is used as a functional layer, a strength of the carbon nanotube layer is large, the flexible sheet will not be damaged due to the carbon nanotube layer no matter of how it is bent and pulled, or cleaned.

Depending on the embodiment, certain blocks/steps of the methods described may be removed, others may be added, and the sequence of blocks may be altered. It is also to be understood that the description and the claims drawn to a method may comprise some indication in reference to certain blocks/steps. However, the indication used is only to be viewed for identification purposes and not as a suggestion as to an order for the blocks/steps.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A soft physiotherapy instrument, comprising:
    a flexible sheet and a controller configured to control the flexible sheet, the flexible sheet comprises:
        a first flexible layer;
        a second flexible layer overlapped with the first flexible layer;
        a plurality of functional layers sandwiched between the first flexible layer and the second flexible layer, wherein each of the plurality of functional layers comprises a carbon nanotube layer, the carbon nanotube layer comprises a plurality of carbon nanotubes uniformly distributed in the carbon nanotube layer; and
        a plurality of electrodes, wherein two ends of each of the plurality of electrodes are separately electrically connected with a pair of the plurality of functional layers, the flexible sheet is electrically coupled with the controller via the plurality of electrodes.

2. The soft physiotherapy instrument of claim 1, wherein the first flexible layer or the second flexible layer defines a window, and the plurality of electrodes are exposed from the window and electrically connected to the controller.

3. The soft physiotherapy instrument of claim 1, wherein a material of the first flexible layer or the second flexible layer is non-woven fabric, silk, flexible cloth, porous flexible paper, or silica gel.

4. The soft physiotherapy instrument of claim 1, wherein the carbon nanotube layer comprises a carbon nanotube film or a plurality of carbon nanotube films overlapped with each other.

5. The soft physiotherapy instrument of claim 4, wherein the carbon nanotube film is a freestanding film.

6. The soft physiotherapy instrument of claim 5, wherein the carbon nanotube film comprises a plurality of successive and oriented carbon nanotubes joined end-to-end by van der Waals attractive force therebetween.

7. The soft physiotherapy instrument of claim 6, wherein the carbon nanotube film comprises a plurality of successively oriented carbon nanotube segments joined end-to-end by van der Waals attractive force therebetween, and each carbon nanotube segment comprises a plurality of carbon nanotubes substantially parallel to each other, and joined by van der Waals attractive force therebetween.

8. The soft physiotherapy instrument of claim 5, wherein the carbon nanotube film comprises a plurality of carbon nanotubes entangled with each other.

9. The soft physiotherapy instrument of claim 5, wherein the carbon nanotube film comprises a plurality of carbon nanotubes joined by van der Waals attractive force, an angle between a primary alignment direction of the carbon nanotubes and a surface of the carbon nanotube film is ranged from 0 degrees to 15 degrees.

10. The soft physiotherapy instrument of claim 1, wherein the carbon nanotube layer comprises at least one carbon nanotube wire, the at least one carbon nanotube wire comprises a plurality of successive carbon nanotube segments joined end to end by van der Waals attractive force therebetween and oriented along a length direction of the at least one carbon nanotube wire.

11. The soft physiotherapy instrument of claim 10, wherein the carbon nanotube layer comprises one carbon nanotube wire, the carbon nanotube wire is bended to form the carbon nanotube layer.

12. The soft physiotherapy instrument of claim 10, wherein the carbon nanotube layer comprises a plurality of carbon nanotube wires crossed or weaved with each other.

13. The soft physiotherapy instrument of claim 1, wherein a material of the plurality of electrodes is metal, alloy, indium tin oxide (ITO), antimony tin oxide (ATO), conductive silver paste, conductive polymer or conductive carbon nanotube.

14. The soft physiotherapy instrument of claim 1, wherein a middle part of each of the plurality of electrodes is electrically connected to the controller.

15. The soft physiotherapy instrument of claim 1, wherein a circuit is formed by the controller, two of the plurality of electrodes, the plurality of functional layers electrically connected with the two of the plurality of electrodes, and skin of the user.

16. A method for using soft physiotherapy instrument, the method comprising:
    providing a soft physiotherapy instrument, the soft physiotherapy instrument comprises a flexible sheet and a controller, wherein the flexible sheet comprises:
        a first flexible layer;
        a second flexible layer overlapped with the first flexible layer;
        a plurality of functional layers sandwiched between the first flexible layer and the second flexible layer, wherein each of the plurality of functional layers comprises a carbon nanotube layer, the carbon nanotube layer comprises a plurality of carbon nanotubes uniformly distributed in the carbon nanotube layer; and
        a plurality of electrodes, wherein two ends of each of the plurality of electrodes are separately electrically connected with a pair of the plurality of functional layers, the flexible sheet is electrically coupled with the controller via the plurality of electrodes;
    applying the flexible sheet on a user's skin; and
    turning on the controller and selecting a function button on the controller, inputting a current to the plurality of functional layers in the flexible sheet, and the user's skin with the current.

17. The method of claim 16, wherein a voltage is applied on two electrodes and kept for a power-on time and stop for a dwell time on the two electrodes, and then the voltage is applied to another two electrodes.

18. The method of claim 17, wherein K is the numbering of each electrode, the voltage is applied to the two electrodes in an order 1 and 2, 2 and 3, 3 and 4 . . . K-1 and K.

19. The method of claim 18, wherein two pairs of functional layers corresponding to each two electrodes are cyclically input current, and the skin corresponding the two pairs of functional layers are cyclically stimulated.

\* \* \* \* \*